United States Patent
Theofilos (10) Patent No.: US 8,425,613 B2
(45) Date of Patent: Apr. 23, 2013

(54) EXPANDABLE INTERVERTEBRAL IMPLANT

(75) Inventor: Charles Theofilos, Palm Beach Gardens, FL (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 13/154,175

(22) Filed: Jun. 6, 2011

(65) Prior Publication Data
US 2011/0301714 A1 Dec. 8, 2011

Related U.S. Application Data

(60) Provisional application No. 61/351,668, filed on Jun. 4, 2010.

(51) Int. Cl.
*A61F 2/44* (2006.01)
*A61B 17/88* (2006.01)

(52) U.S. Cl.
USPC ......................... 623/17.16; 606/279

(58) Field of Classification Search .................. 606/246, 606/249, 279, 326, 90, 105; 623/17.11, 17.15, 623/17.16
See application file for complete search history.

(56) References Cited

U.S. PATENT DOCUMENTS

| | | |
|---|---|---|
| 4,599,086 A | 7/1986 | Doty |
| 4,860,746 A | 8/1989 | Yoon |
| 5,290,312 A | 3/1994 | Kojimoto et al. |
| 5,571,192 A | 11/1996 | Schönhöffer |
| 5,776,198 A | 7/1998 | Rabbe et al. |
| 5,989,290 A | 11/1999 | Biedermann et al. |
| 6,200,348 B1 | 3/2001 | Biedermann et al. |
| 6,322,562 B1 | 11/2001 | Wolter |
| 6,610,090 B1 | 8/2003 | Böhm et al. |
| 7,285,134 B2 | 10/2007 | Berry et al. |
| 7,655,025 B2 | 2/2010 | Ritland |
| 2005/0283248 A1 | 12/2005 | Gordon et al. |
| 2008/0021555 A1 | 1/2008 | White et al. |
| 2011/0106260 A1 | 5/2011 | Laurence et al. |

OTHER PUBLICATIONS

International Search Report and Written Opinion of the International Searching Authority mailed Sep. 28, 2011 in counterpart International Application No. PCT/US2011/039288 filed Jun. 6, 2011.

*Primary Examiner* — Jan Christopher Merene
*Assistant Examiner* — David Comstock
(74) *Attorney, Agent, or Firm* — Carter, DeLuca, Farrell & Schmidt, LLP (57) ABSTRACT

An intervertebral implant assembly includes first and second support members and a retention member. The first and second support members are configured to engage first and second vertebral bodies, respectively. The first and second support members define first and second guide portions, respectively. In particular, the first and second support members are slidably movable relative to each other. The retention member includes a face plate and an arm member extending from the face plate. The arm member is disposed between the first and second support members to maintain a relative position of the first and second support members. The face plate defines an access through hole in communication with the first and second guide portions.

21 Claims, 6 Drawing Sheets

EXPANDABLE INTERVERTEBRAL IMPLANT

CROSS-REFERENCE TO RELATED APPLICATION

This application claims priority to, and the benefit of, U.S. Provisional Patent Application No. 61/351,668, filed on Jun. 4, 2010, the entire contents of which are hereby incorporated by reference herein.

BACKGROUND

1. Technical Field

The present disclosure relates to an apparatus for treating spinal conditions, and, more particularly, to an expandable intervertebral implant and a method of use therefor.

2. Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as inter-vertebral discs. Inter-vertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of a part of the lamina, i.e., the bony roof of the spinal canal. Discectomy involves removal of the inter-vertebral discs. Corpectomy involves removal of the vertebral body as well as the adjacent inter-vertebral discs.

A number of spinal surgical devices may be used to promote bony fusion after decompressing the spinal nerves. For instance, surgeons often replace the diseased vertebral tissue with one or more spinal cages and bone support matrix. Spinal cages support adjacent vertebral segments, while furthering spinal fusion of adjacent vertebral bodies. Scientists and clinicians have developed a number of devices and methods for decompressing spinal nerves. Improvements to this methods and devices are nevertheless still possible.

Furthermore, intervertebral spacer implants used as a stand-alone device or provided in an assembly including a retention mechanism to help alleviate expulsion and movement of the implant when placed in the spine, are well known. Such implant assemblies are advantageous in providing an implant that is easier to insert in the spine. Such implant assemblies resist expulsion subsequent to implantation. Intervertebral spacer implant assemblies which include a spacer and a plate, where the plate comprises a supplemental or alternative retention mechanism having one or more holes in the anterior end of the plate that are directed toward the superior, inferior or both endplates of adjacent vertebrae are also known in the art. Such implants are used to stabilize and immobilize the spinal segments in the treatment of single or multi-level degenerative disc disease, spinal stenosis, and failed previous fusions, as well as other spine conditions.

One problem with such implant assembly/face plate combinations is that it is necessary to provide and inventory a plurality of sizes of both implants and face plates in order to accommodate the sizes required to treat a broad sampling of the patient population. Accordingly, a need exists for an implant assembly that can accommodate various dimensions of intervertebral space with reduced number of parts.

SUMMARY

In accordance with an embodiment of the present disclosure, there is provided an intervertebral implant assembly including first and second support members and a retention member. The first and second support members are configured to engage first and second vertebral bodies, respectively. The first and second support members are slidably movable relative to each other. The first and second support members define first and second guide portions, respectively. The retention member includes a face plate and an arm member extending from the face plate. The arm member is disposed between the first and second support members to maintain a relative position of the first and second support members. The face plate defines an access through hole in communication with the first and second guide portions.

The first support member may include a base plate and an extension member extending from the base plate. The second support member may define a bore dimensioned to slidably receive at least a portion of the extension member of the first support member therein. The guide portions may be defined at a respective peripheral portion of the first and second support members. The access through hole may be defined by arcuate and dished curvilinear sidewalls.

In addition, the arm member of the retention member may engage the extension member of the retention member when interposed between the first and second support members. The first and second guide portions may each be defined in a peripheral portion of the respective first and second support members. Each guide portion may define a groove providing a desired trajectory of bone screw into the respective vertebral body. The face plate of retention member may at least partially cover the first and second guide portions.

The intervertebral implant assembly may further include a pair of bone screws, wherein the access through hole is adapted and dimensioned to receive the pair of bone screws. In particular, one of the pair of bone screws inserted through the access through hole may be secured to the first vertebral body through the first guide portion, and the other of the pair of bone screws is secured to the second vertebral body through the second guide portion.

Head portions of the bone screws may lockingly engage each other in the access through hole. In addition, at least one of the pair of bone screws may include a thread below a seat surface of the bone screw, whereby the thread deforms a portion of the sidewall of the access through hole.

In an embodiment, an intervertebral implant assembly may further include a retention clip disposed within the access through hole to retain the bone screws therein. The retention clip may be in a shape of a bent open eight. In addition, the retention clip may be elastic.

In accordance with another aspect of the present disclosure, there is provided a method of securing adjacent vertebral bodies. The method includes providing an intervertebral implant assembly including first and second support members configured to engage first and second vertebral bodies, respectively, and a retention member including a face plate and an arm member extending from the face plate. In particular, the first and second support members define first and second guide portions, respectively. The first and second support members are slidably movable relative to each other. In addition, the face plate defines an access through hole in communication with the first and second guide portions. The arm member is disposed between the first and second support members to maintain a relative position of the first and second support members. The method further includes distracting adjacent vertebral bodies, inserting the first and second support members between the first and second vertebral bodies, positioning the retention member between the first and second support members to maintain the relative position of the first and second support members, and inserting a plurality of bone screws through the face plate and into the respective vertebral bodies.

The method may further include removing vertebral tissue. In addition, inserting a plurality of bone screws through the face plate and into the respective vertebral bodies may include inserting a pair of bone screws into the first and second vertebral bodies through first and second guide portions, respectively.

The intervertebral implant assembly may further include a retainer clip disposed within the access through hole. The retainer clip may have a bent open eight shape.

BRIEF DESCRIPTION OF THE DRAWINGS

Various embodiments of the present disclosure are described hereinbelow with reference to the drawings, wherein.

DETAILED DESCRIPTION OF EMBODIMENTS

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 1:
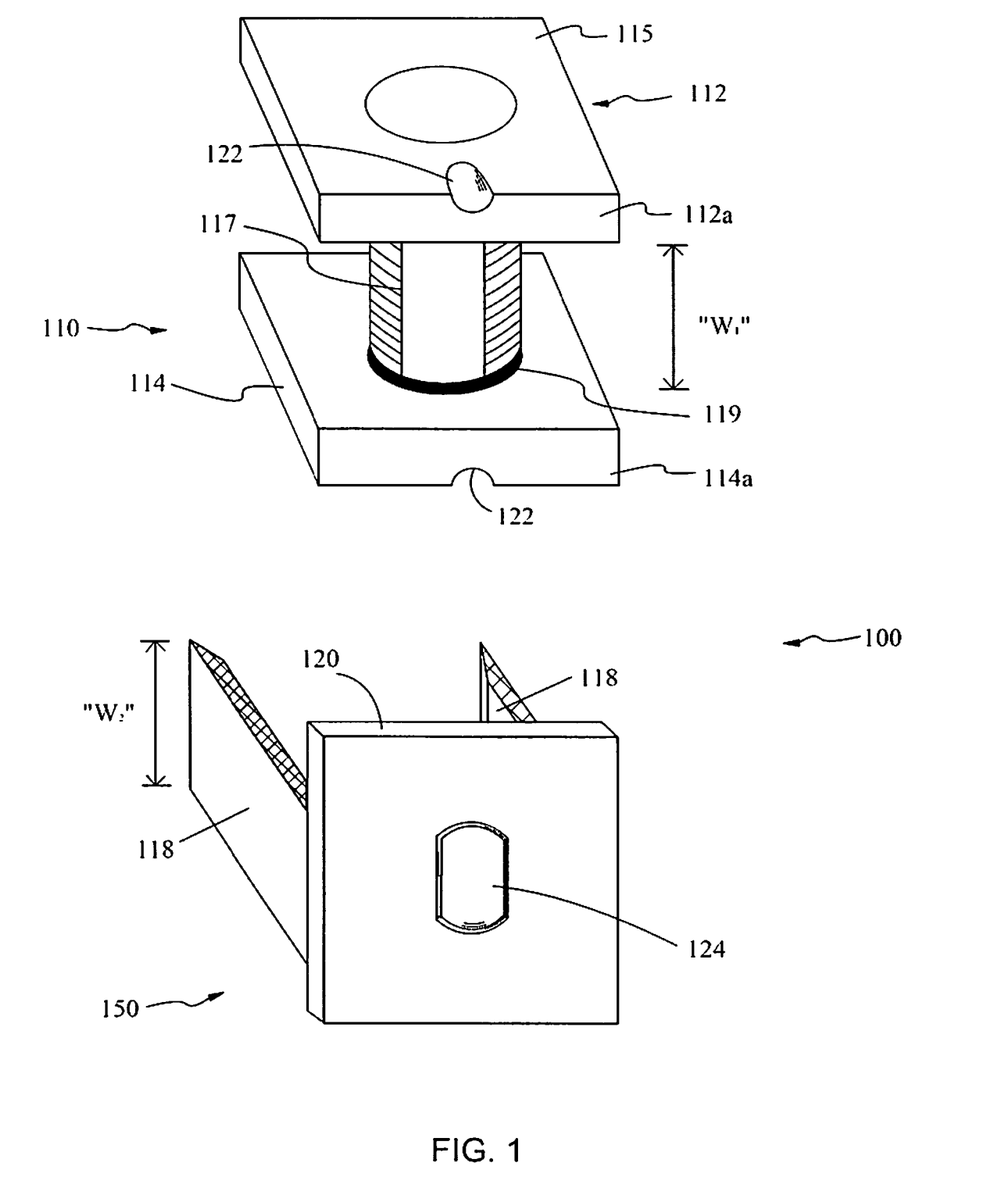
FIG. 1 is a perspective view of an expandable intervertebral implant assembly in accordance with an embodiment of the present disclosure with parts separated.

With reference to FIG. 1, an embodiment of the present disclosure is shown generally as an expandable intervertebral implant assembly 100 configured and adapted to be positioned between vertebral bodies 50, 52 (FIG. 2) to support vertebral bodies 50, 52 and to promote spinal fusion. Expandable intervertebral implant assembly 100 includes an expandable member 110 and a retention member 150. Expandable member 110 in conjunction with retention member 150 enables the user to adjust expandable member 110 to various dimensions of the intervertebral space, as will be discussed below. Expandable member 110 and retention member 150 may be made of titanium, titanium alloy, stainless steel, allograft bone, autologous bone graft, polyetheretherketone (PEEK), cobalt chrome, polymeric materials, a combination thereof, or any other suitable biocompatible material. In particular, expandable member 110 may formed of bone, or an artificial material other than bone which may be harder or stronger than bone, such as, e.g., ceramic materials. Expandable member 110 may include a bone growth promoting material such as, e.g., bone morphogenic protein and hydroxyapatite.

Figure 2:
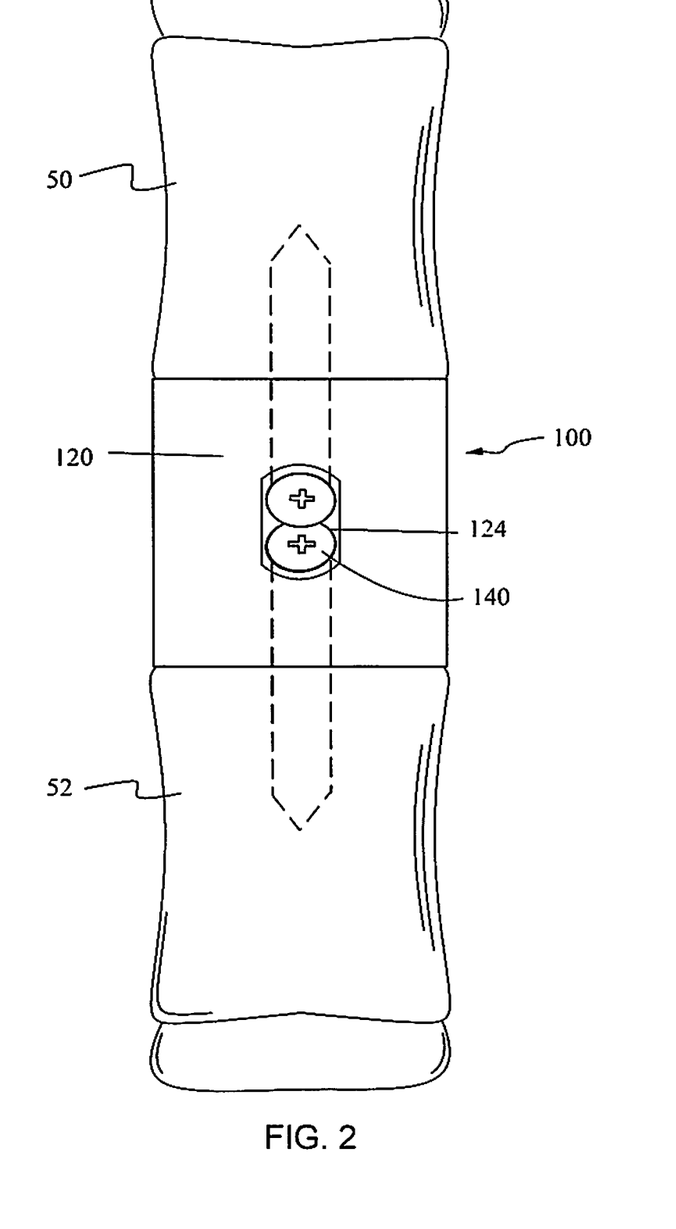
FIG. 2 is a front view of the implant assembly of FIG. 1 interposed between vertebral bodies.

With continued reference to FIG. 1, expandable member 110 includes a first support member 112 and a second support member 114. First support member 112 includes a base member 115 and an adjustment member 117 extending from base member 115. Second support member 114 defines a bore 119 dimensioned to slidably receive therein at least a portion of adjustment member 117. In this manner, the distance "$W_1$" between base plate 115 of first support member 112 and second support member 114 may be adjusted by slidably moving adjustment member 117 within bore 119. In addition, first and second support members 112, 114 each include a lateral surface adapted to engage respective vertebral bodies 50, 52. In addition, first and second support members 112, 114 each include respective proximal edges 112a, 114a. Proximal edges 112a, 114a each define a guide portion 122. Guide portion 122 is dimensioned to engage a bone screw 140 (FIG. 2). In particular, each guide portion 122 defines a groove providing a desired trajectory of bone screw 140 into vertebral body 50, 52. Furthermore, each guide portion 122 leads into respective lateral surfaces that engage vertebral bodies 50, 52.

Retention member 150 includes a base plate 120 and a pair of legs 118 extending from base plate 120. The pair of legs 118 is specifically dimensioned so that legs 118 are positionable between first and second support members 112, 114 to maintain a desired separation of first and second support members 112, 114. In addition, base plate 120 is dimensioned to precisely cover the area defined by proximal edges 112a, 114a of base member 115 and second support member 114, respectively. The pair of legs 118 is disposed between first and second support members 112, 114 when expandable member 110 is positioned between desired vertebral bodies 50, 52. In this manner, a desired distance "$W_1$" between base member 115 of first support member 112 and second support member 114 may be effected through selectively choosing the desired width "$W_2$" of the pair of legs 118.

With reference now to FIGS. 1 and 2, base plate 120 defines an elongated access through hole 124 adapted and dimensioned to receive therethrough bone screws 140. In particular, access through hole 124 is defined by arcuate and dished curvilinear sidewalls, whereby the tightening of bone screws 140 within access through hole 124 forces the screw head and the arcuate and curvilinear sidewalls of access through hole 124 into locking engagement with one another when fully seated.

With particular reference now to FIG. 2, access through hole 124 is adapted and dimensioned to receive a pair of bone screws 140. Arcuate and dished curvilinear sidewalls of access through hole 124 form a locking engagement with two bone screws 140. In particular, one of the two bone screws 140 is driven into the inferior vertebral body 52 and the other bone screw 140 is driven into the superior vertebral body 50, as shown in phantom. Under such configuration, bone screws 140 are in a single plane common to both the superior and inferior vertebral bodies 50, 52.

Access through hole 124 may define an exit aperture (not shown), which may be integrally defined with access through hole 124 or defined within a metallic insert that includes a spherical or semi-spherical curvilinear wall for each bone screw 140. Such configuration provides variation in bone screw 140 trajectory and increased contact between bone screw 140 and base plate 120.

Figure 3:
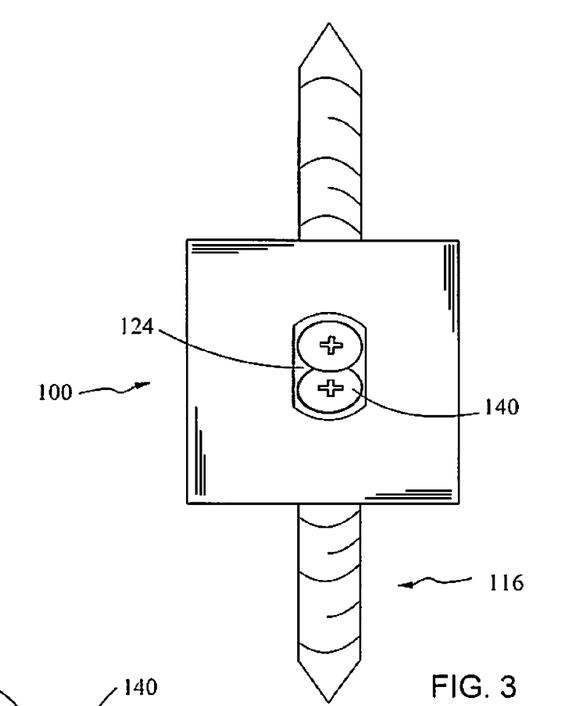
FIG. 3 is a front view of the implant assembly having bone screws inserted therethrough.
Figure 4:
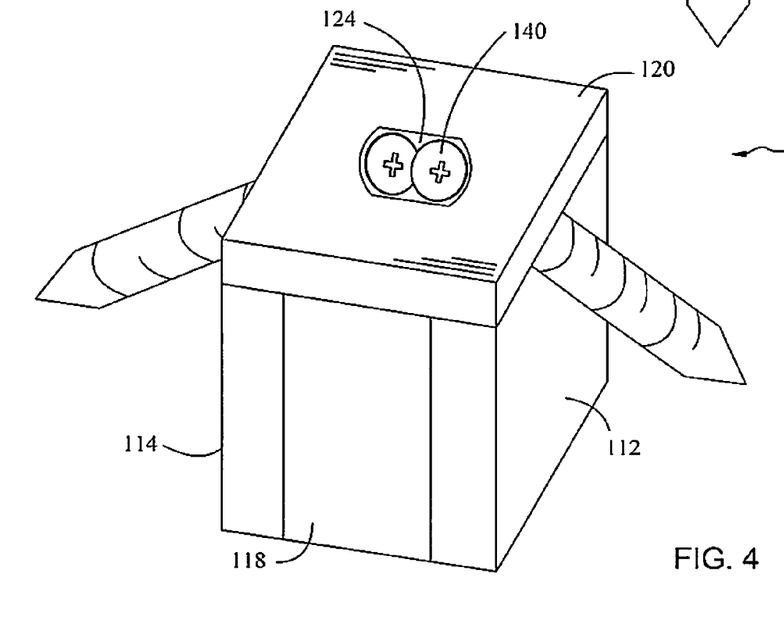
FIG. 4 is a perspective view of the implant assembly of FIG. 3.

With reference now to FIGS. 2-4, bone screws 140 are first inserted via access through hole 124 and follow the trajectory delineated by guide portions 122 which facilitates insertion of bone screws 140 into respective inferior and superior vertebral bodies 50, 52.

Figure 5:
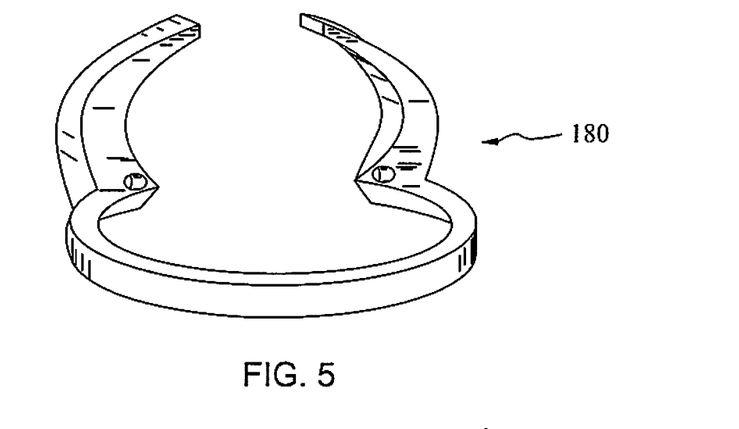
FIG. 5 is a perspective view of a bone screw retainer clip for use with the implant assembly of FIG. 1.
Figure 6:
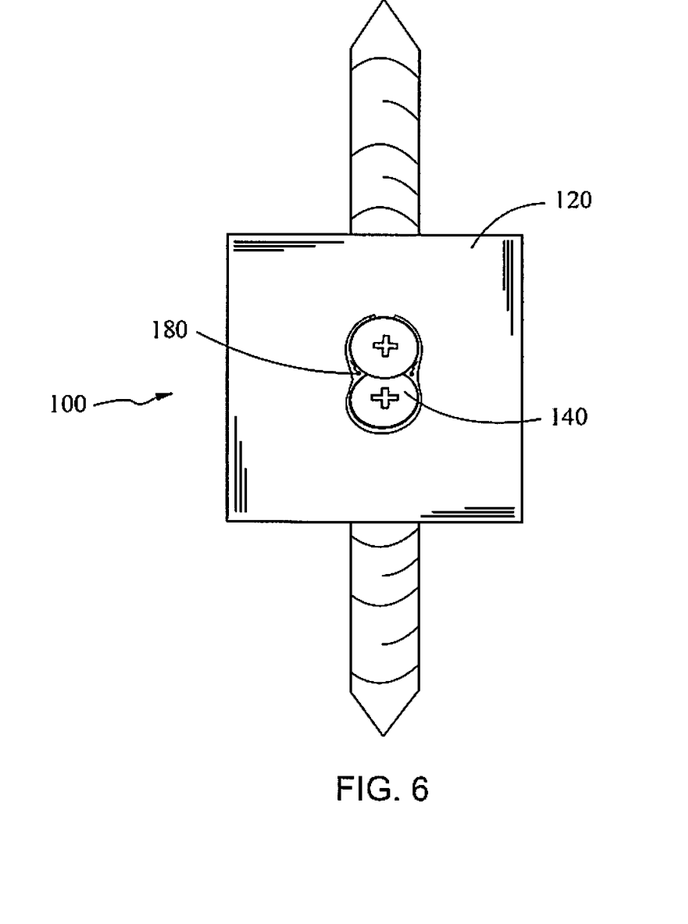
FIG. 6 is a front view of the implant assembly of FIG. 3 including the bone screw retainer clip of FIG. 5 mounted therein.

With reference now to FIGS. 5 and 6, a screw retainer clip 180 may be further utilized as an additional safety measure to guard against bone screw 140 separation in the event of accidental backing out or breakage of bone screws 140. Screw retainer clip 180 has a shape of a "bent open eight." Screw retainer clip 180 is placed in a pre-defined groove in the sidewalls of access through hole 124. Retainer clip 180 may be initially compressed by a tool (not shown) and inserted into access through hole 124 to engage the pre-defined groove. Subsequent to compression of clip 180 and insertion into access through hole 124, retainer clip 180 and retention member 150 form a unitary assembly. Each of bone screw 140 can be inserted individually in their respective apertures. Retainer clip 180 is designed to deflect and enable the heads of bone screws 140 to pass therethrough, and then return to its prior position to inhibit bone screw 140 from falling out of access through hole 124 should it become loosened.

Figure 7:
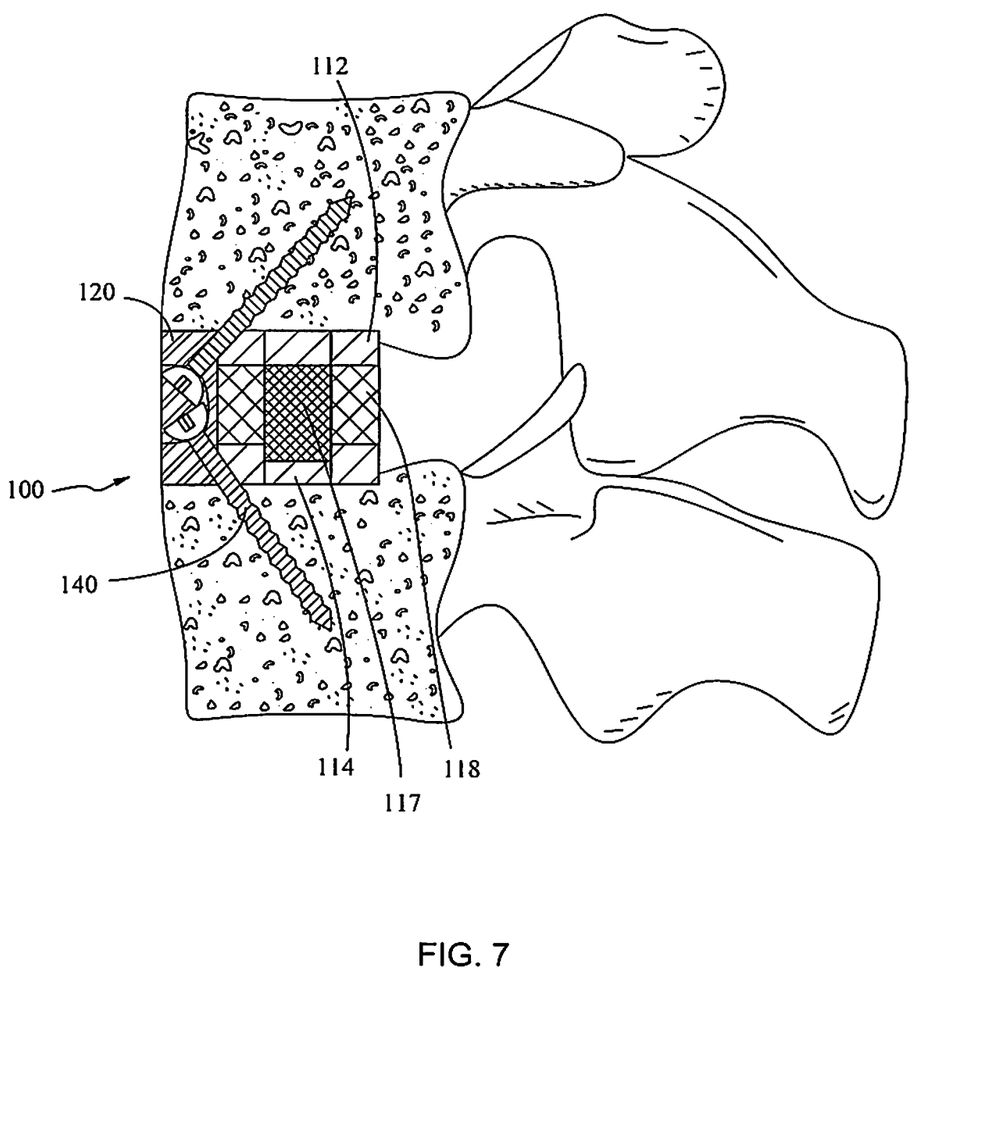
FIG. 7 is a longitudinal cross-sectional view of the implant assembly of FIG. 1 securely positioned between the vertebral bodies by the bone screws.

With brief reference to FIG. 7, it is contemplated that bone screw 140 may include a spherical or semi-spherical head with a substantially flat upper surface, such that the spherical surface of one of the pair of bone screws 140 engages the top surface of the other of the pair of bone screws 140 regardless of the trajectory of the pair of bone screws 140. In this manner, a reliable head-to-head contact independent of bone screw 140 trajectories is achieved.

It is further contemplated that expandable intervertebral implant assembly 100 may be part of a kit including expandable member 110 and several combination retention members 150 with various dimensions, in order to accommodate various intervertebral spaces. Retention members 150 with various dimensions enable the user to maintain first and second supporting members 112, 114 in different relative positions.

In use, the surgeon first distracts vertebral bodies 50, 52 of interest to establish the intervertebral space. The surgeon may then remove vertebral tissue, if necessary or desired. At this time, the surgeon positions expandable member 110 between desired vertebral bodies 50, 52. The surgeon can determine the desired relative positions of first and second support members 112, 114 and insert a corresponding retention member 150 therebetween to retain the relative positions of base member 115 and second support member 114. Thereafter, the surgeon can secure implant assembly 100 to the vertebral bodies 50, 52 to inhibit expulsion or malpositioning by inserting a plurality of bone screws 140 through access through hole 124 of retention member 150 and into the inferior and superior vertebral bodies 50, 52, respectively, as best illustrated in FIG. 7.

Figure 8:
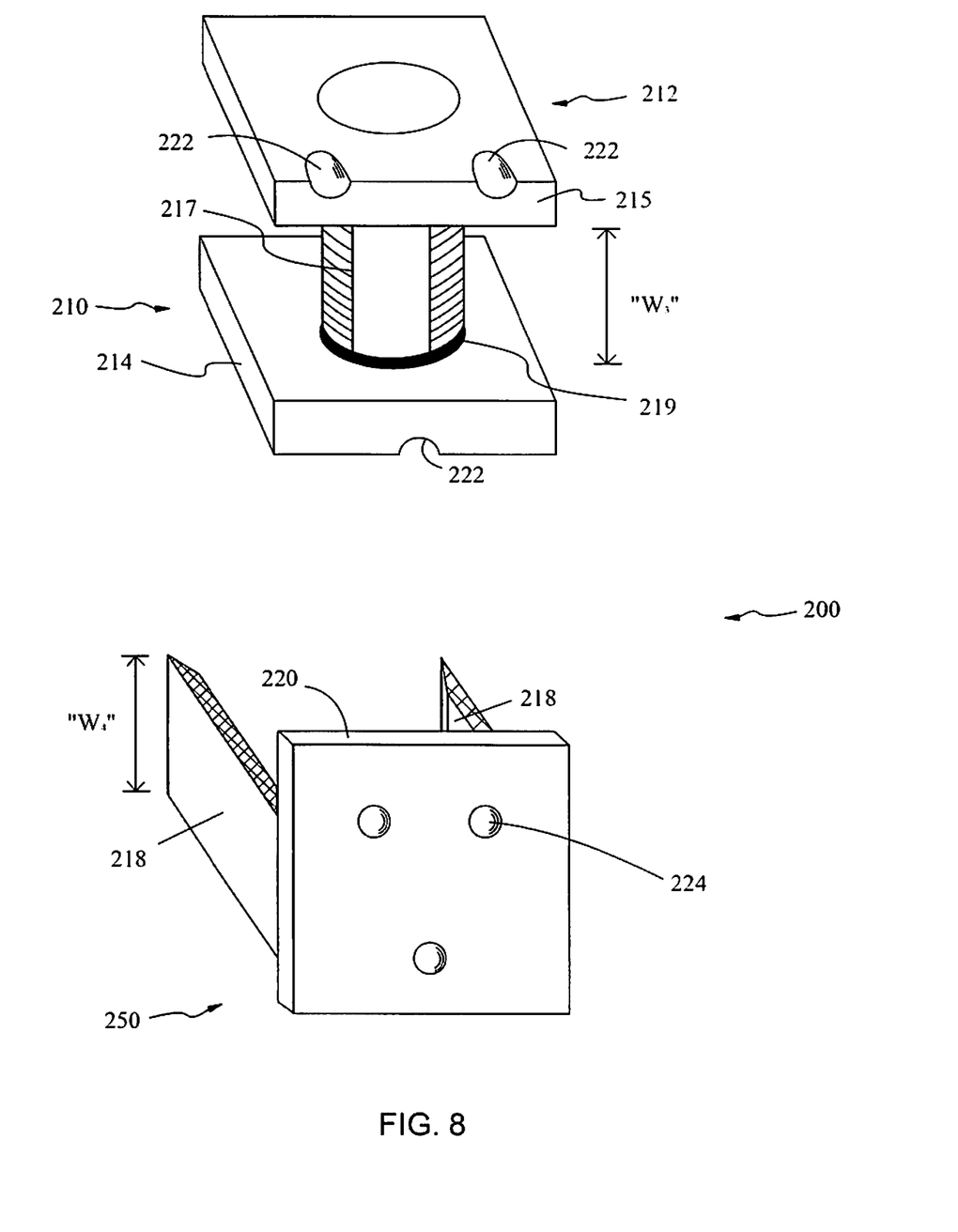
FIG. 8 is a perspective view of an expandable intervertebral implant assembly in accordance with another embodiment of the present disclosure with parts separated.

With reference now to FIG. 8, another embodiment of expandable intervertebral implant assembly 200 is illustrated. In the interest of brevity, the present embodiment will focus on the difference between the previously described implant assembly 100 and implant assembly 200. Implant assembly 200 is configured and adapted to be positionable between vertebral bodies 50, 52 to support vertebral bodies 50, 52 and to promote spinal fusion. Implant assembly 200 includes an expandable member 210 and a retention member 250. Expandable member 210 in conjunction with retention member 250 enables the user to adjust expandable member 210 to be adaptable to various dimensions of the intervertebral space.

With continued reference to FIG. 8, expandable member 210 includes a first support member 212 and a second support member 214. First support member 212 includes a base member 215 and an adjustment member 217 extending from base member 215. Second support member 214 defines a bore 219 dimensioned to slidably receive therein at least a portion of adjustment member 217. First and second support members 212, 214 each include a lateral surface adapted to engage endplates of respective vertebral bodies 50, 52. First and second support members 212, 214 each define a guide portion 222 dimensioned to engage bone screw 140. In particular, each guide portion 222 defines a groove providing a desired trajectory of bone screws 140 into vertebral bodies 50, 52.

Base member 215 of first support member 212 defines a pair of guide portions 222 and second support member 214 defines a single guide portion 222. The pair of guide portions 222 defined in first support member 212 leads into the lateral surface of the first support member 212 that engages the superior vertebral body 50, and the single guide portion 222 defined in second support member 214 leads into the lateral surface of second support member 214 that engages the inferior vertebral body 52. Accordingly, under such configuration, a single bone screw 140 is driven into an inferior vertebral body 52 and a pair of bone screws 140 is driven into the superior vertebral body 50.

Retention member 250 includes a base plate 220 and a pair of legs 218 extending from base plate 220. In contrast to base plate 120 of implant assembly 100, base plate 220 defines a plurality of access through holes 224 adapted and dimensioned to receive therethrough bone screws 140. Each access through hole 224 is dimensioned to receive a single bone screw 140. Each through hole 224 is defined by arcuate and dished curvilinear sidewalls, whereby the tightening of bone screw 140 within access through hole 224 forces the screw head and the arcuate and curvilinear sidewalls of access through hole 124 into locking engagement with one another when fully seated. It is contemplated that any number of bores 224, guide portions 222, and bone screws 140 may be utilized to meet the need of a particular surgical procedure being performed.

It is further envisioned that access through hole 224 may be threaded or smooth. The head of bone screws 140 may also may be threaded or smooth. In addition, bone screws 140 may be made of a material that is harder than the material of the sidewalls that define access through hole 224 and/or the metallic insert that defines the exit aperture. For example, bone screw 140 may be made of titanium alloy (e.g., Ti-6Al-4V) and the sidewalls and/or the metallic insert may be made of a relatively softer compatible material, such as a softer titanium material (e.g. commercially pure titanium). Under such configuration, thread of bone screw 140 deforms the sidewalls and/or the metallic insert and secures bone screw 140 therewith as bone screw 140 is advanced through access through hole 224 and/or the exit aperture, thereby inhibiting loosening of bone screw 140. This type of screw locking arrangement is described in U.S. Pat. No. 6,322,562 to Wolter, which is incorporated by reference herein in its entirety.

It is further contemplated that first and second support members 212, 214 may include facets (not shown) for enhanced gripping of vertebral bodies 50, 52, as well as a plurality of teeth or ridges (not shown) or similar projections to aid in securing implant assembly 100 to vertebral bodies 50, 52. In addition, a portion of the expandable member 210 may be tapered to facilitate insertion thereof through the intervertebral space and provide an amount of lordosis.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. An intervertebral implant assembly comprising:
   a first support member configured to engage a first vertebral body, the first support member defining a first guide portion;
   a second support member configured to engage a second vertebral body, the second support member defining a second guide portion, the first and second support members slidably movable relative to each other; and
   a retention member including a face plate and an arm member extending from the face plate, the arm member disposed between the first and second support members to maintain a relative position of the first and second support members, the face plate defining an access through hole configured to receive a bone screw therethrough, wherein the first and second guide portions each define a groove configured to receive at least a portion of the bone screw inserted through the access through hole and direct the bone screw towards the respective vertebral bodies.

2. The intervertebral implant assembly according to claim 1, wherein the first support member includes a base plate and an extension member extending from the base plate, the second support member defining a bore dimensioned to slidably receive at least a portion of the extension member of the first support member therein.

3. The intervertebral implant assembly according to claim 2, wherein the guide portions are defined at a respective peripheral portion of the first and second support members.

4. The intervertebral implant assembly according to claim 3, wherein the arm member of the retention member engages the extension member of the retention member when the retention member is interposed between the first and second support members.

5. The intervertebral implant assembly according to claim 1, wherein the access through hole is defined by arcuate and dished curvilinear sidewalls.

6. The intervertebral implant assembly according to claim 1, wherein the guide portions are each defined in a peripheral portion of the respective first and second support members.

7. The intervertebral implant assembly according to claim 1, wherein the face plate of retention member at least partially covers the first and second guide portions.

8. The intervertebral implant assembly according to claim 1, further comprising a pair of bone screws, wherein the access through hole is adapted and dimensioned to receive the pair of bone screws.

9. The intervertebral implant assembly according to claim 8, wherein one of the pair of bone screws inserted through the access through hole is secured to the first vertebral body through the first guide portion, and the other of the pair of bone screws is secured to the second vertebral body through the second guide portion.

10. The intervertebral implant assembly according to claim 9, wherein head portions of the bone screws lockingly engage each other in the access through hole.

11. The intervertebral implant assembly according to claim 8, wherein at least one of the pair of bone screws include a thread below a seat surface of the bone screw, whereby the thread deforms a portion of the side wall of the access through hole.

12. The intervertebral implant assembly according to claim 1, further comprising a retention clip disposed within the access through hole to retain the bone screws therein.

13. The intervertebral implant assembly according to claim 12, wherein the retention clip has a shape of a bent open eight.

14. The intervertebral implant assembly according to claim 12, wherein the retention clip is elastic.

15. The intervertebral implant assembly according to claim 1, wherein the first and second guide portions are configured to provide a desired trajectory of the bone screw towards the respective vertebral body.

16. A method of securing adjacent vertebral bodies, comprising:
   providing an intervertebral implant assembly including:
      first and second support members configured to engage first and second vertebral bodies, respectively, the first and second support members defining first and second guide portions, respectively, the first and second support members slidably movable relative to each other; and
      a retention member including a face plate and an arm member extending from the face plate, the arm member disposed between the first and second support members to maintain a relative position of the first and second support members, the face plate defining an access through hole in communication with the first and second guide portions;
   distracting adjacent vertebral bodies;
   inserting the first and second support members between the first and second vertebral bodies;
   positioning the retention member between the first and second support members to maintain the relative position of the first and second support members; and
   inserting a plurality of bone screws through the face plate and into the respective vertebral bodies.

17. The method according to claim 16, further comprising removing vertebral tissue.

18. The method according to claim 16, wherein inserting a plurality of bone screws through the face plate and into the respective vertebral bodies includes inserting a pair of bone screws into the first and second vertebral bodies through first and second guide portions, respectively.

19. The method according to claim 18, wherein head portions of the bone screws lockingly engage each other in the access through hole.

20. The method according to claim 16, wherein the intervertebral implant assembly further includes a retainer clip disposed within the access through hole.

21. The method according to claim 20, wherein the retainer clip has a bent open eight shape.

\* \* \* \* \*

UNITED STATES PATENT AND TRADEMARK OFFICE
CERTIFICATE OF CORRECTION

PATENT NO. : 8,425,613 B2  
APPLICATION NO. : 13/154175  
DATED : April 23, 2013  
INVENTOR(S) : Charles Theofilos Page 1 of 1

It is certified that error appears in the above-identified patent and that said Letters Patent is hereby corrected as shown below:

On the title page  
item (73) Assignee should read: Spartan Cage, LLC., Palm Beach Gardens, FL (US)

Signed and Sealed this  
Twenty-fourth Day of December, 2013

Margaret A. Focarino  
*Commissioner for Patents of the United States Patent and Trademark Office*